(12) United States Patent
Miller

(10) Patent No.: US 11,642,503 B2
(45) Date of Patent: May 9, 2023

(54) TREATMENT OF SKIN AND SKIN CONDITIONS USING SNAILS

(71) Applicant: Judith D. Miller, Camby, IN (US)

(72) Inventor: Judith D. Miller, Camby, IN (US)

( * ) Notice: Subject to any disclaimer, the term of this patent is extended or adjusted under 35 U.S.C. 154(b) by 798 days.

(21) Appl. No.: 16/585,675

(22) Filed: Sep. 27, 2019

(65) Prior Publication Data

US 2020/0100481 A1    Apr. 2, 2020

Related U.S. Application Data

(60) Provisional application No. 62/738,571, filed on Sep. 28, 2018.

(51) Int. Cl.
*A61K 35/618* (2015.01)
*A61M 35/00* (2006.01)

(52) U.S. Cl.
CPC ......... *A61M 35/003* (2013.01); *A61K 35/618* (2013.01)

(58) Field of Classification Search
None
See application file for complete search history.

(56) References Cited

U.S. PATENT DOCUMENTS

| | | | | |
|---|---|---|---|---|
| 5,538,740 A | * | 7/1996 | Abad | A61K 8/987 424/59 |
| 2010/0233111 A1 | * | 9/2010 | Wang | A61K 35/618 424/94.1 |
| 2018/0064635 A1 | * | 3/2018 | Min | A61K 8/65 |

FOREIGN PATENT DOCUMENTS

| | | | |
|---|---|---|---|
| CN | 101181221 | * | 5/2008 |
| EP | 3124030 | * | 2/2017 |
| WO | WO 2021/080519 | * | 4/2021 |

OTHER PUBLICATIONS

McDermott, M. et al. Advancing Discovery of Snail Mucins Function and Application. Frontiers in Bioengineering and Biotechnology 9:734023, Oct. 2021. (Year: 2021).*

Onzo, A. et al. Untargeted Analysis of Pure Snail Slime . . . J of Mass Spectrometry 56(5)1-7, May 2021. (Year: 2021).*

* cited by examiner

*Primary Examiner* — Ralph J Gitomer
(74) *Attorney, Agent, or Firm* — Maginot, Moore & Beck LLP

(57) ABSTRACT

The method for a skin treatment using a first snail on a human patient includes placing the first snail on a first surface to allow the first snail to attach itself to the first surface. The method further includes projecting a first predetermined amount of a first agent onto the first snail with to cause the first snail to secrete a liquid on the first surface. The method further includes administering the secreted liquid over a surface of a skin of a portion of a body of the human patient.

16 Claims, 3 Drawing Sheets

TREATMENT OF SKIN AND SKIN CONDITIONS USING SNAILS

RELATED APPLICATIONS

This application claims priority to U.S. Provisional Application No. 62/738,571, filed Sep. 28, 2018, the content of which in its entirety is hereby incorporated by reference.

TECHNICAL FIELD

This disclosure relates generally to a system and method for the enhancing the treatment of the skin, in particular this disclosure relates to the enhancing the treatment of the skin using excretions of snails for the skin treatments.

BACKGROUND

Snails produce different kinds of excretions, secretions, slime, or mucus that, among other things, allow the snails to crawl and also prevent the desiccation of exposed soft tissues. Particularly, snails have at least eight different glands that secrete different types of fluid. Four glands secrete a mucus or mucin, one gland secretes a protein, one gland secretes calcium carbonate granules, another a pigmented secretion and a fourth that releases fat globules. Different parts of the snail excrete different kinds of mucus. For example, the foot of the snail excretes a mucus with a protein that helps propel the snail across the surface of the skin. The side of the foot of the snail excretes "Type A" and "Type B" mucus and the sole of the foot exudes "Type C" and "Type D" mucus. The "Type C" and "Type D" mucus is excreted from the sole of the foot have adhesive and lubricating properties that allow the snail to adhere to surfaces while moving along the surface by undulation of the foot. As such, only a portion of the snail excretion, secretion, slime, or mucus may have antioxidant properties and may stimulate collagen production in the human skin that can lead to reductions in wrinkles and enhanced wound healing.

Snail excretions have been used in skin treatments for many years. For example, snail excretions have been incorporated into creams that a consumer can then apply to his/her skin. In another example, clients are offered "snail facial" skin treatments where the snails are directly placed onto the skin of the client and allowed to crawl across the face of the client, leaving behind the slime on the client's face used for the skin treatment. However, these treatments and the "snail facial" apply mostly the "Type C" and "Type D" mucus that are secreted from the sole of the foot to allow the snail to adhere to the surface and crawl along the surface. Furthermore the "snail facial" may not allow for targeted application of snail mucin in specific locations of the body of the client since the snail has a free range to travel where it wants. Moreover, there are certain locations on the client's body that may not be accessed by the crawling snail.

Therefore, there is needed a method to enhance the effects of snail excretions applied on the skin using a different combination of the mucus excreted by the snails.

SUMMARY

An exemplary method for skin treatment using a first snail on a human patient includes placing a first snail on a first surface to allow the first snail to attach itself to the first surface. The method further includes projecting a first predetermined amount of a first agent onto the first snail to cause the first snail to secrete a liquid on the first surface. The method further includes administering the secreted liquid over a surface of a skin of a portion of a body of the human patient.

The exemplary method further includes disengaging the first snail from a second surface by grasping the shell of the first snail between a finger and a thumb of a user performing the method. The second surface includes a surface of at least one of a container, a terrarium, and an aquarium. The exemplary method further includes allowing the applied secreted liquid to be absorbed by the skin by at least one of rubbing a first apparatus over the skin, exposing the skin to a second apparatus, and exposing the skin to a second agent for a first predetermined time.

An exemplary device for performing a skin treatment using a first snail includes a control unit operatively connected to a microcontroller, a placement device, using the microcontroller, configured to receive a first signal from the control unit and place the first snail on a first surface and allow the first snail to attach itself to the first surface, a projecting device, using a microcontroller, configured to receive a second signal from the control unit and project a first predetermined amount of a first agent onto the first snail to cause the first snail to excrete a liquid on the first surface, and an application device, using the microcontroller, configured to receive a third signal from the control unit and apply the secreted liquid over a surface of a skin.

Another exemplary device for a skin treatment using a first snail includes a microcontroller and a control unit operatively connected to the control unit. The control unit includes a projecting device, using a microcontroller, configured to project a first predetermined amount of a first agent onto the first snail to cause the first snail to excrete a liquid on the first surface after the first snail is placed on a first surface and allowed to attach itself to the first surface.

DETAILED DESCRIPTION

For the purposes of promoting an understanding of the principles of the embodiments described herein, reference is now made to the drawings and descriptions in the following written specification. No limitation to the scope of the subject matter is intended by the discussion of any one embodiment. This disclosure also includes any alterations and modifications to the illustrated embodiments and includes further applications of the principles of the described embodiments as would normally occur to one skilled in the art to which this document pertains, including the combination, substitution, or non-inclusion of various features from various embodiments.

Snails have a mantle, which is a fold of the skin that surrounds the snail's internal organs. The mantle appears at the interface between the front of the foot and the shell. The mantle of the snail includes glands that secrete protein, calcium, pigment and "Type A" and "Type B" mucus. A portion of the secretion from the glands protect the snail's body by moisturizing the snail to prevent the tissue from drying out. The composition of secretion from the mantle is different than the composition of secretion exuded from the foot.

Figure 1:
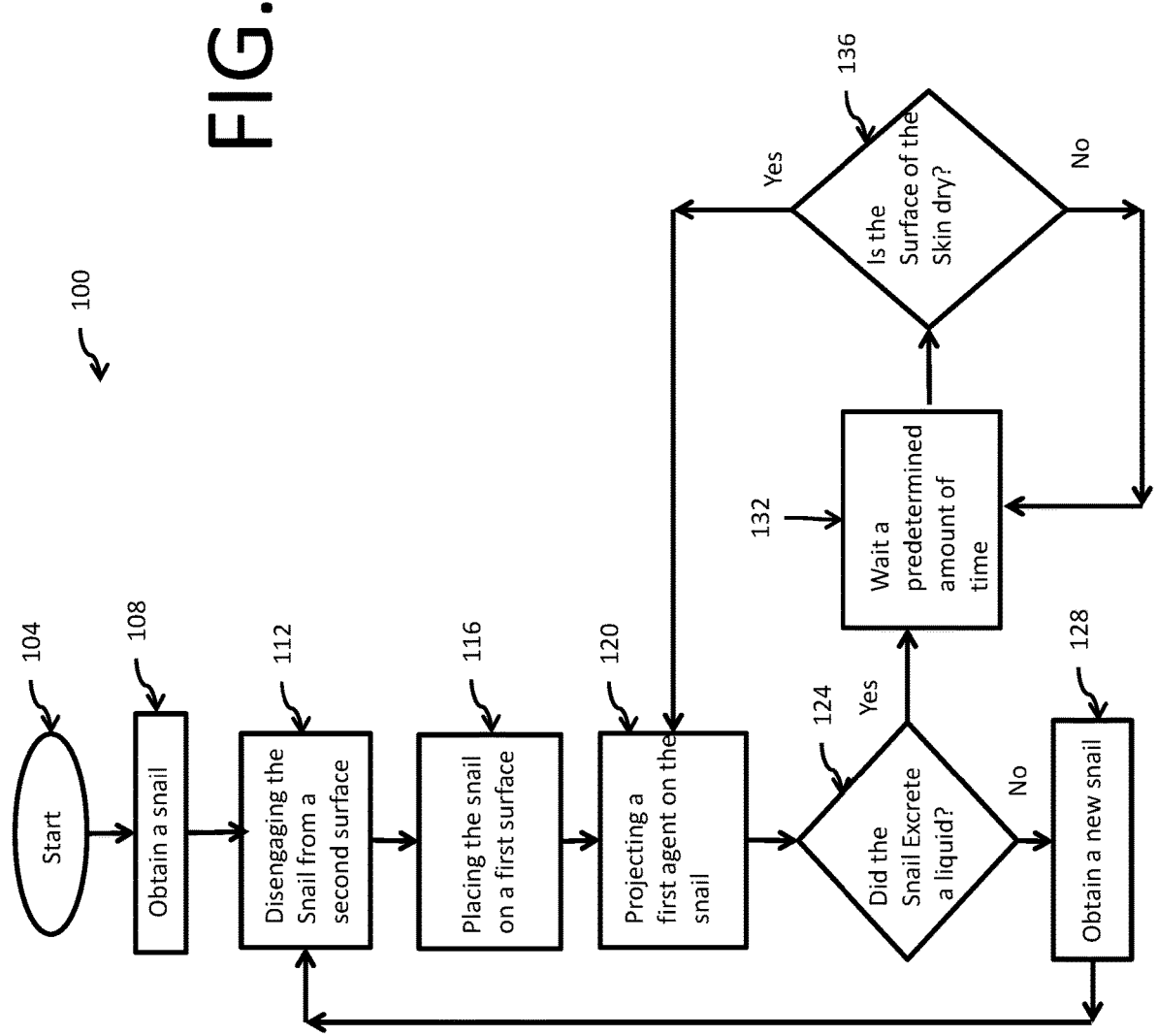
FIG. 1 illustrates an embodiment of a method for enhancing a skin treatment using the excretions from the snail.

FIG. 1 illustrates an embodiment of a method for enhancing a skin treatment using the excretions from the snail 240. In a preferred embodiment, this skin treatment method 100 uses a beneficial combination of excretions exuded from the mantle of the snail 240 for the skin treatment. As illustrated in FIG. 1 and with reference to FIG. 2, this skin treatment method 100 includes sanitizing or cleaning at least one of the hands of the person or device performing the facial, the face of the client or the human patient, the snail 240, or the like. (Step 104). A snail 240 is obtained to perform the skin treatment. (Step 108). The snail 240 could be garden snail 240 or a *Helix aspersa* or any other variety of gastropod that secretes mucus to be used for the skin treatment. It should be understood that while a snail 240 is used in this embodiment for performing the skin treatment, any other animal that secretes mucus can be used for performing the skin treatment.

As further illustrated in FIG. 1, the snail 240 is disengaged from a second surface. (Step 112). In one example, the aesthetician 228, user, or the person performing the skin treatment carefully removes the snail 240 from a second surface. In another example, a device can be used to carefully remove the snail 240 from the second surface. The second surface can include the snail's 240 container such as terrarium or aquarium, or the like. The person removes the snail 240 gently and carefully so as to not damage the shell, cause stress to the snail 240, traumatize the snail 240, or the like. Preferably, the snail 240 can be gently grasped by the shell between a finger and the thumb of the aesthetician 228 or another person assisting in the skin treatment process 100 and carefully removed from the second surface. In one example, the snail 240 can be disengaged from the second surface by gently lifting the snail 240 from the rear end or the back of the snail 240. For example, the snail 240 can be disengaged from the second surface by first disengaging the rear end of the snail 240 from the second surface.

According to one embodiment of the skin treatment process 100, the snail 240 is placed onto a first surface. (Step 116). This skin treatment method 100 can be carried out by the aesthetician 228, another person assisting the skin treatment process, the client, a placement device 216, or the like. The first surface can include the thumb or another body part of the aesthetician 228, another person, a body part of the client, a plate, a specially designed surface, a material designed to absorb the secreted liquid from the snail 240, a material designed to absorb and process the secreted liquid from the snail 240, leaves, flowers, or the like. In one example, once the snail 240 is placed on the first surface and the snail 240 is allowed to attach itself onto the first surface. In another example, the snail 240 does not attach itself or is unable to attach itself onto the first surface, for example, because of the properties of material of the first surface.

As further illustrated in FIG. 1, a first agent 236 is projected onto the snail 240. (Step 120). The exposure to the first agent 236 can allow the snail 240 to extend from its shell. Once the snail 240 is out of the shell, the glands of the mantle of the snail 240 will begin to secrete a liquid. In one example, the snail 240 is exposed to the first agent 236 for a predetermined amount of time. In one example, the snail 240 is misted with water as the first agent 236. The snail 240 can be exposed to the first agent 236 for a duration of 1 millisecond to 5 minutes. In another example, the snail 240 is exposed to the first agent for 1 millisecond to 1 hour. In one example, a first predetermined amount of the first agent 236 is projected onto the snail 240. For example, a first predetermined amount of the first agent 236 can include between about 0.1 milliliter to about 1 milliliter of the first agent 236. In another example, a first predetermined amount of the first agent 236 can include between about 0.1 milliliter to about 5 milliliters of the first agent 236. The first agent 236 could be water, oil, heat, different forms of light therapy, or any other combination of solutions. The first agent 236 could be projected onto the snail 240 in the form of a mist or any other form, applied directly onto the snail 240, or exposed to the snail 240 in its environment. It should be understood that any other method of exposing the snail 240 to the first agent 236 can be used. For example, a projecting device 212 can be used to project the first agent 236 onto the snail 240, apply the first agent 236 onto the snail 240, or expose the snail 240 to the first agent 236.

As further illustrated in FIG. 1, the skin treatment method 100 determines whether the snail 240 excreted a liquid, secretion, mucus, or slime, or the like 244. (Step 124). If the snail 240 did not excrete any liquid 244, then the snail 240 can be exposed again to the first agent 236 (Step 120) or a new snail can be obtained (Step 128). If the snail 240 did excrete liquid 244, the liquid 244 may have been secreted on the first surface such as the thumb of the aesthetician 228. The secreted liquid 244 can then be applied onto the skin of client 232. (Step 132). For example, in this step 124, the snail 240 is still latched to the thumb of the aesthetician 228 and exuding liquid 244 and the aesthetician's hand 228 can glide over the client's skin 232 to administer or apply the liquid 244 onto the skin. In another example, an application device 220 can be used to apply the secreted liquid 244 onto the surface of the skin 232. It should be understood that the secreted liquid 244 can be used in another manner for skin treatment or any other purpose. In one example, the secreted liquid 244 can be placed in a pill to be ingested for skin treatment or any other treatment. In another example, the secreted liquid 244 is further processed and added into facial creams, masks, facial sprays, pills, food, drinks, or the like.

With further reference to FIG. 1, in one embodiment of the skin treatment method 100, the aesthetician 228, a person assisting with the treatment, or a determining device 224 determines whether the secreted liquid 244 from the snail 240 has been applied to the required portion of the surface of skin of the client. (Step 142). For example, this step 142 will determine whether the secreted liquid 244 has been applied to the whole face, face and neck, or a certain portion of a body part of the client. In one example, if the skin treatment method 100 is being used to remove a wart or treat a skin condition, then this step 142 will determine whether the secreted liquid 244 has been applied to the portion of the body or all of portions of the body having the skin condition.

If the secreted liquid 244 has not been applied to the required portion of the skin of the client 232, then the skin treatment method 100 determines whether the snail 240 is continuing to secrete the liquid 244. (Step 146) If the snail 240 is continuing to secrete the liquid 244, the secreted liquid 244 is continued to be applied onto the skin of the client 232. If the snail is not continuing to secrete the liquid 244, then the aesthetician 228, a person assisting with the treatment, or a determining device 224 determines whether the snail 240 has retracted into its shell. (Step 150). If the snail 240 has retracted into its shell, then the snail 240 is again exposed to the first agent (Step 120) or exposed to another agent in order to enable the snail 240 the extend from its shell. If the snail 240 has not retracted into its shell, then a new snail can be obtained (step 128) and the skin treatment process 100 continues by disengaging the new snail from a second surface (step 112).

As further illustrated in FIG. 1, if the secreted liquid 244 has been applied to the skin of the client 232, then the skin treatment process 100 determines whether the surface of the skin is dry. (Step 136). In one example, either the aesthetician 228 or another person or even a determining device 224 can be used to determine whether the surface of the skin 232 in dry. In one example, this step 136 alternatively determines whether a predetermined amount of time has passed since the last application of the secreted liquid 244 on the surface of the skin 232 instead of checking whether the secreted liquid 244 has dried up. In another example, this step 136 determines whether a predetermined percentage of the applied secreted liquid 244 is soaked into the skin. In another example, this step 136 determines whether the secreted liquid 244 on the surface of the skin 232 is dry to a predetermined percentage. For example, the step 136 determines whether 50% of the applied secreted liquid 244 is dry and 50% of the applied secreted liquid 244 is still moist on the surface of the skin 232. In other example, the step 136 determines whether between 80% to 100% of the applied secreted liquid is dry. In one example, the applied secreted liquid 244 is allowed to be absorbed by the skin or soaked into the skin by rubbing a first apparatus such as a massaging unit over the skin, exposing the skin to a second apparatus such as light or heat therapy, or even exposing the skin to a second agent such as air, another chemical, oil, heat, light, or the like for a first predetermined time. The first predetermined time can include between 1 second to 1 hour.

As further illustrated in FIG. 1, when step 136 determines that the surface of the skin 232 is not dry or any other condition required after the application of the secreted liquid 244 is not met, then the skin treatment method 100 moves to step 138, where the aesthetician 228, another person, or a determining device 224 waits for a predetermined time before rechecking in step 136 whether the condition is met. (Step 138). If the condition required in step 136 is met (for example, if the surface of the skin 232 is dry 85%), then the skin treatment method 100 moves to step 154 where it is determined whether the required length and duration of the skin treatment time has passed. (Step 154). The length and duration of the treatment time can vary depending upon the skin condition being treated. For example, a treatment for reducing wrinkles may require a shorter treatment time than a treatment for acne, wart, or another skin condition. If the required length and duration of the skin treatment time has not passed, then the applied secreted liquid 244 can be rehydrated with a third agent such as a mist of distilled water to maintain the efficacy of the snail slime for the desired treatment time or for a second predetermined. In another example, the applied secreted liquid 244 is exposed to the third agent for a second predetermined time such as between 1 second to 5 minutes. In one example, if the required skin treatment time has not passed, then facial exercises can be performed on the skin of the client 232 or the skin of the client 232 can be exposed to different forms of light therapy, heat, or other agents.

As further illustrated in FIG. 1, if the required length and duration of the skin treatment has passed (step 154), then the skin of the client 232 can now be carefully cleaned to remove any of the applied secreted liquid 244.

The method 100 can further include providing the snail 240 with food or diet to alter the composition of the secretions. For example, the snail 240 can be provided with plant food such as diet of kale, lettuce, and other leafy greens. Plant food can enable the snail 240 to provide an optimum quantity and quality of secretions needed for the skin treatment. In another example, the food of the snail 240 can be changed differently during the method 100 to provide different kinds of composition of secretion. In another example, the food of the snail 240 can be changed depending upon the skin treatment being offered, the type of the client's skin, and/or reaction of the client's skin to the composition of the secretions.

The skin treatment method 100 illustrated in FIG. 1 can allow more than just the foot secretions of the snail to reach the skin of the client. For example, the method 100 allows the mantle exudate of the snail 240 to be used for the treatment of the client's skin condition. As such, this method 100 may allow a higher amount a more beneficial compounds from the mucus applied towards the skin treatment. For example, this method 100 may allow a higher amount of "Type A" and "Type B" mucus applied towards the treatment of the client's skin condition, then "Type C" and "Type D" mucus. This method 100 may also allow the aesthetician 228 to target certain locations of the client's body and skin for treatment and apply a limited amount of the secreted liquid 244, mucin, or a processed form of the secreted liquid 244 onto a specific spot on the client. The method 100 can be used to target different skin conditions such as warts, scars, wounds, and other isolated areas of damage to the client's skin.

It should be understood that while an exemplary embodiment of the skin treatment 100 is disclosed, the selection of the preferred method may be influenced by factors such as the skin treatment being performed, the reaction of the snail 240 to the skin treatment method 100 during the skin treatment, the reaction of the client's skin to the skin treatment method 100, the type of skin of the client, or the like. Furthermore, the steps of the exemplary skin treatment method 100 may be combined in various ways; some of these steps may be optional and may be omitted.

Figure 2:
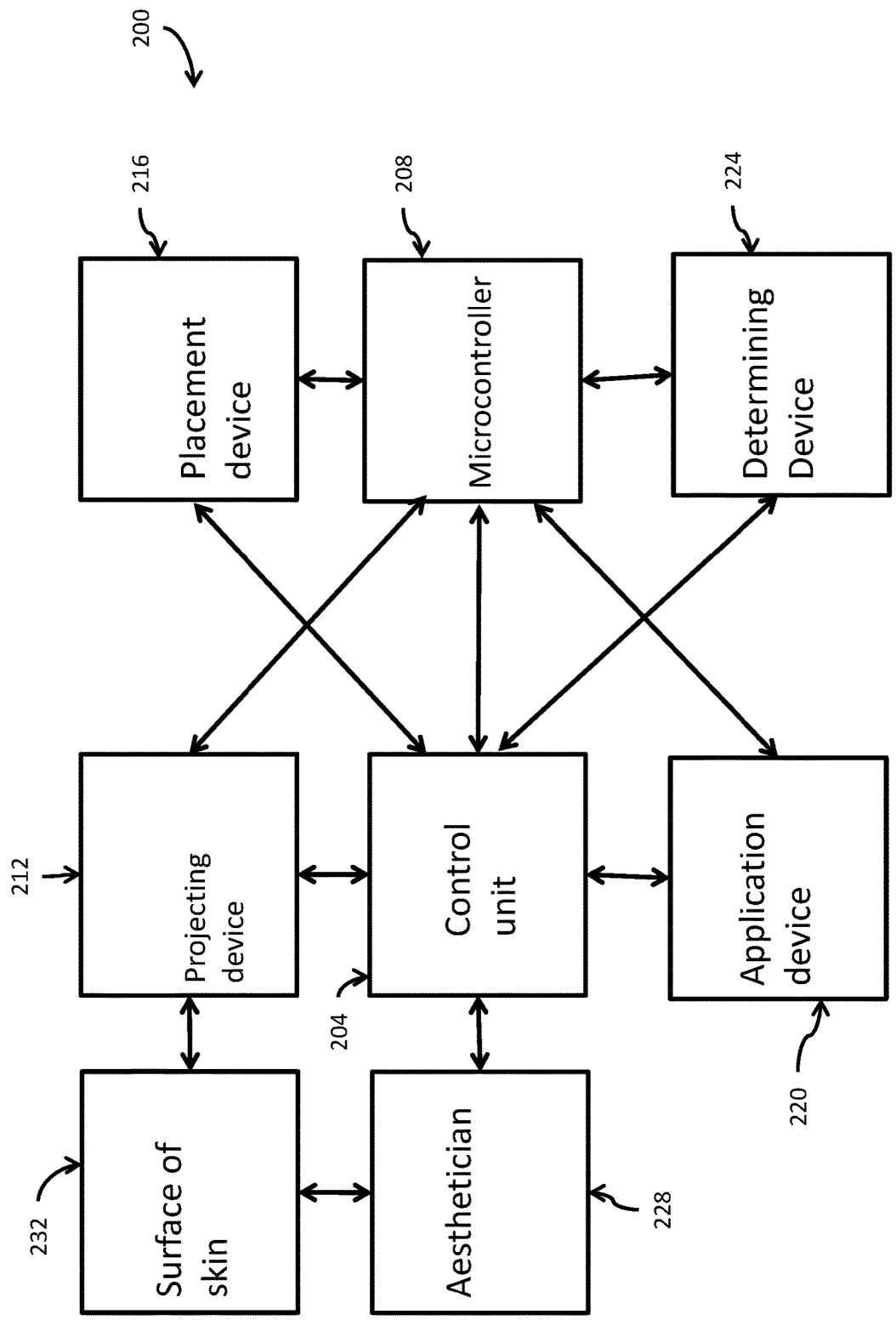
FIG. 2 illustrates an exemplary embodiment of a device configured to perform the skin treatment method.

FIG. 2 illustrates an exemplary embodiment of a device 200 configured to perform the skin treatment method 100. The device 200 includes a control unit 204 that interfaces with an aesthetician 228 or another person assisting with the skin treatment. The control unit 204 also interfaces with a microcontroller 208. The device 200 includes a placement device 216 configured to place a snail 240 onto a first surface. The control unit 204 transmits a first signal to the placement device 216 to enable the placement device 216 to obtain another snail and place the other snail onto the first surface. The control unit 204 transmits a fifth signal to the placement device 216 to enable the placement device 216 to obtain another snail and place the other snail onto the first surface. The device 200 further includes a projecting device 212 configured to project a first agent 236 onto the snail 240 or expose the snail 240 to the first agent 236 so that the snail 240 can secrete liquid 244 that can be applied onto the surface of the client's skin 232. In one example, the control unit 204 transmits a second signal to the projecting device 212 after a third predetermined time to enable the projecting device 212 to project a first predetermined amount of the first agent 236 onto the snail 240 and a fourth signal to the projecting device 212 to project the first agent 236 onto the snail 240 a second time after the snail 240 has retracted back into its shell. The first predetermined amount can depend upon the type of skin treatment being offered, the skin type of the client, the quality and quantity of liquid that the snail 240 is secreting, or the like. In one example, a first predetermined amount of the first agent 236 is projected onto the snail 240. For example, a first predetermined amount of the first agent 236 can include between about 0.1 milliliter to about 1 milliliter of the first agent 236. In another example, a first predetermined amount of the first agent 236 can include between about 0.1 milliliter to about 5 milliliters of the first agent 236. The third predetermined time can be immediately, when the aesthetician 228 or another user indicates they ready or the snail 240 is placed before the projecting device 212, or the like. The device 200 further includes an application device 220 to apply the secreted liquid 244 onto the skin of the client 232. The control unit 204 transmits a third signal to the application device 220 to enable the application device 220 to apply the secreted liquid 244 onto the skin of the client 232. The device 200 further includes a determining device 224 that determines at least one of whether the snail 240 excrete a liquid 244 (step 124), whether the required portion of the client's skin has been covered with the secreted liquid 244 (step 146), whether the snail 240 has retracted into its shell (step 150), whether the surface of the skin is dry (step 136), or whether the required duration of skin treatment has passed (step 154). The control unit 204 interfaces with the determining device 224 by transmitting and receiving signals to enable the determining device to carry out certain steps of the method of the method 100. These devices 204, 212, 220, 216, 224 interface with the microcontroller 208 to execute the skin treatment method 100. The control unit 204 executes software stored in memory and interfaces with the devices 212, 220, 216, 224 based on the instructions from the software and the inputs from the aesthetician 228, the client, or any other person assisting with the skin treatment 100. It should be understood that the client, aesthetician 228, or any other person assisting with the skin treatment can interface with any combination of these devices 204, 212, 220, 216, 224. Additionally, the determining device 224 can include sensors to detect whether the client's face has absorbed the secreted liquid 244, whether the applied secreted liquid 244 is dry on the client's face, the reaction of the applied secreted liquid 244, whether the client is having any adverse reactions to the secreted liquid 244, whether the snail 240 is exhibiting any signs of stress or other symptoms that can affect the quality and quantity of the secreted liquid 244, or the like.

Figure 3:
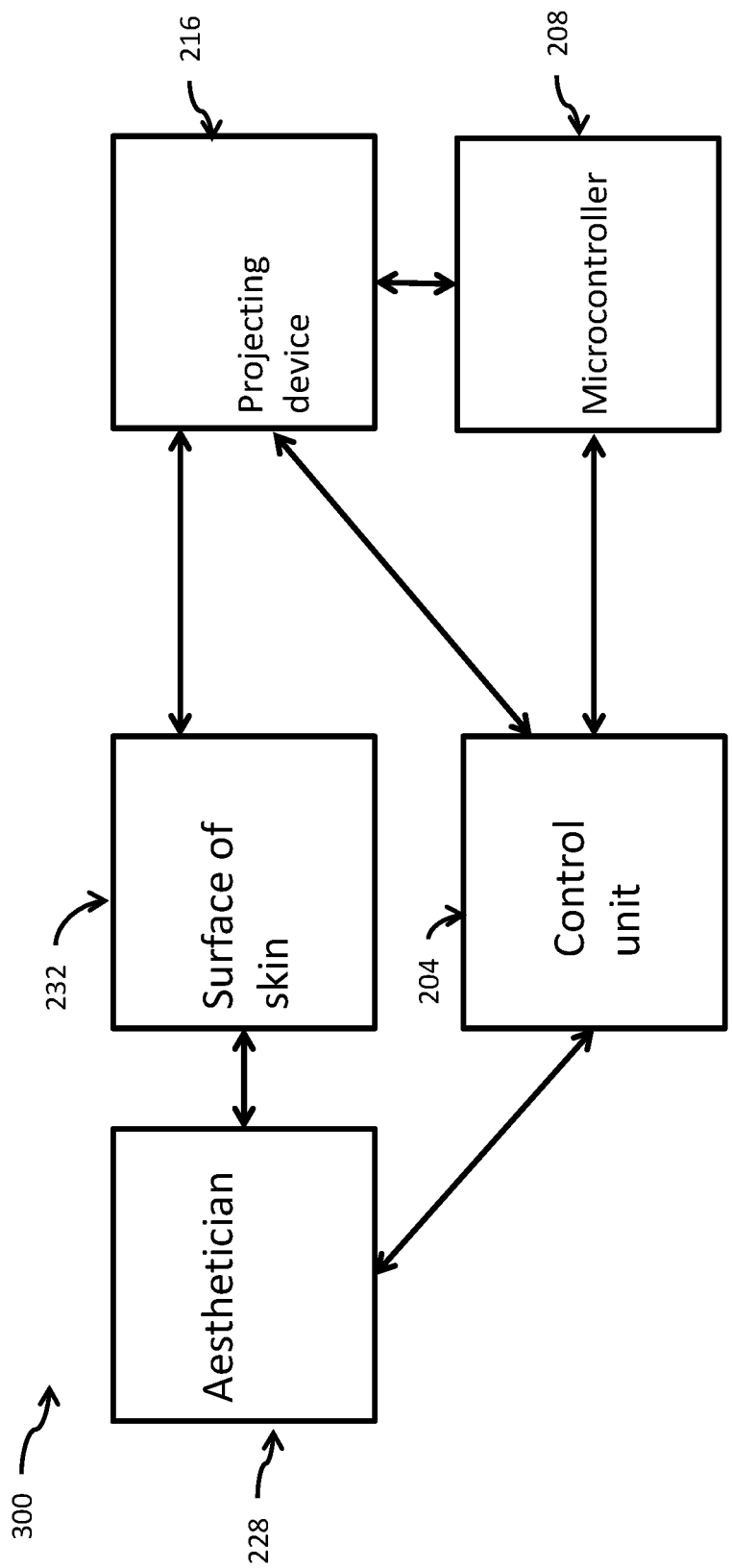
FIG. 3 illustrates another exemplary embodiment of a device configured to perform the skin treatment method.

FIG. 3 illustrates an exemplary embodiment of a device 300 configured to perform the skin treatment method 100. The device 300 includes a control unit 204 and a microcontroller 208 configured to execute software stored in memory in order to perform the skin treatment procedure 100. For example, the control unit 204 interfaces with the projecting device 216 to project a first agent 236 onto the snail in order to extract secreted liquid 244 on the first surface. The aesthetician 228 may use the projecting device 216 instead of her own hands in order to avoid contaminating her hands while performing the skin treatment procedure 100. In one example, the aesthetician 228 may interface with the control unit 204 using voice, gestures, or the like while her hands are busy performing the skin treatment procedure 100.

Although an exemplary skin treatment method 100 and embodiment of the devices 200, 300 have been described; it may be evident that various modifications and changes may be made to these embodiments without departing from the broader spirit and scope of the disclosure. Accordingly, the specification and drawings are to be regarded in an illustrative rather than a restrictive sense.

The exemplary devices 200, 300 include a microcontroller 208 or a microprocessor (such as a central processing unit (CPU), a graphics processing unit (GPU) or both), a main memory and a static memory, which communicate with at least one other via buses. The exemplary devices 200, 300 can further include a video display unit (such as a liquid crystal display (LCD) screen) and an alphanumeric input device (such as a keyboard), a user interface (UI) navigation device (such as a mouse), a disk drive unit, a signal generation device (such as a speaker) and a network interface device. The disk drive unit can include a machine-readable medium on which is stored one or more sets of instructions and data structure utilizing any combination of the method described herein. The software can be transmitted or received over a network using network interface devices that utilizes any number of transfer protocols such as HTTP, WIFI, Bluetooth etc.

Different embodiments of skin treatment method 100 and devices 200, 300 according to this disclosure can include different combinations of features described above, along with any other advances or modifications that would be obvious to one of ordinary skill in the art. It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the disclosure.

What is claimed is:

1. A method for a skin treatment by applying a snail directly on a human patient, comprising:
   placing the snail on a first surface to allow the snail to attach itself to the first surface, wherein the first surface includes a body part of a person performing the skin treatment on the human patient;
   projecting a first predetermined amount of a water mist onto the snail to cause the first snail to secrete a liquid on the first surface; and
   manipulating the snail, by the person, over a surface of a skin of a portion of a body of the human patient to administer the secreted liquid onto the skin.

2. The method as claimed in claim 1, further comprising:
   disengaging the snail from a second surface, different from said first surface, by grasping a shell of the snail before the placement of the snail on the first surface.

3. The method as claimed in claim 2, wherein disengaging the snail from the second surface includes:
   grasping the shell of the snail between a finger and a thumb of a user performing the method.

4. The method as claimed in claim 2, wherein disengaging the snail from the second surface includes:
   grasping a shell of the snail; and
   lifting the snail from a rear end.

5. The method as claimed in claim 2, wherein the second surface includes a surface of at least one of a container, a terrarium, and an aquarium.

6. The method as claimed in claim 2, wherein the snail is disengaged from the second surface in a manner to avoid damage the shell of the snail and to minimize stress to the snail.

7. The method as claimed in claim 1, wherein the first surface includes a thumb of the user.

8. The method as claimed in claim 1, wherein the water mist is distilled water in a form of a mist.

9. The method as claimed in claim 1, further comprising:
   facilitating absorption of the applied secreted liquid by the skin by at least one of rubbing a first apparatus over the skin, exposing the skin to a second apparatus different from said first apparatus, and exposing the skin to a second agent, different from said first agent, for a first predetermined time.

10. The method as claimed in claim 9, wherein the second agent is air.

11. The method of claim 9, wherein the first apparatus is a tissue massaging unit.

12. The method of claim 9, wherein the second apparatus is one or more of a light therapy unit and a heat therapy unit.

13. The method as claimed in claim 1, further comprising: allowing the applied secreted liquid to dry to touch on the surface of the skin.

14. The method as claimed in claim 1, further comprising: exposing the surface of the skin on which the secreted liquid was applied with a second predetermined amount of a mist of distilled water.

15. The method as claimed in claim 14, wherein the second predetermined amount of the mist of distilled water is sufficient to maintain efficacy of the applied secreted liquid for a second predetermined time.

16. The method as claimed in claim 1, further comprising: providing the snail with a diet to enhance volume of the secreted liquid, wherein the diet includes at least one of kale, lettuce, and leafy greens.

* * * * *